US005948927A

United States Patent [19]
Gunther et al.

[11] Patent Number: 5,948,927
[45] Date of Patent: Sep. 7, 1999

[54] BIS-SILYL TERTIARY AMINES

[75] Inventors: Michael Lee Gunther, Danbury, Conn.; Eric Raymond Pohl, Mt. Kisco, N.Y.

[73] Assignee: Witco Corporation, Greenwich, Conn.

[21] Appl. No.: 09/053,292

[22] Filed: Apr. 1, 1998

[51] Int. Cl.[6] ........................ C07F 7/10
[52] U.S. Cl. ........................ 556/419; 556/418
[58] Field of Search ........................ 556/419, 418

[56] References Cited

U.S. PATENT DOCUMENTS

| | | | |
|---|---|---|---|
| 2,929,829 | 3/1960 | Morehouse . | |
| 4,122,074 | 10/1978 | Pepe et al. . | |
| 4,209,455 | 6/1980 | Pepe . | |
| 5,354,881 | 10/1994 | Chang et al. | 556/419 |
| 5,371,261 | 12/1994 | Wang et al. | 556/419 X |
| 5,420,324 | 5/1995 | Lai et la. | 556/419 |
| 5,610,258 | 3/1997 | Weitzel et al. | 556/419 X |

OTHER PUBLICATIONS

Chemical Abstract AN 116:107869;.
Chemical Abstract AN 115:73746;.
Chemical Abstract AN 116:85459;.
Chemical Abstract AN:112:98818;.
Chemical Abstract AN: 110:39177;.
Chemical Abstract AN:77:20592;.
Chemical Abstract AN 126:200521;.
Chemical Registry No. 166819–69–8;.
Chemical Registry No. 170108–98–2;.
Chemical Registry No. 139451–25–5;.
Chemical Registry No. 139036–25–2;.
Chemical Registry No. 135381–19–0;.
Chemical Registry No. 125322–54–5;.
Chemical Registry No. 76300–99–7;.
Chemical Registry No. 184004–99–7; and
Chemical Registry No. 150177–29–0.

*Primary Examiner*—Paul F. Shaver
*Attorney, Agent, or Firm*—Edward K. Welch, II; Andrew S. Reiskind; Timothy X. Witkowski

[57] ABSTRACT

Bis-silyl tertiary amines of the formula (I) $[((R^1)_bY)_aR^2_{3-a}SiR^3]_2NX$ wherein $R^1$ and $R^2$ are monovalent radicals, $R^3$ is a divalent radical, X is a monovalent carbonyl containing radical, Y is oxygen, nitrogen or sulfur, a=1 to 3, and b=1 or 2 depending upon the valency of Y, provide controlled reactivity, crosslinking and good adhesion

20 Claims, No Drawings

BIS-SILYL TERTIARY AMINES

FIELD OF INVENTION

The present invention relates to novel structures of certain bis-silyl-tertiary amines and the manufacture and use thereof.

BACKGROUND OF THE INVENTION

Aminosilanes have many utilities in the coupling of inorganic material, e.g., silica, siliceous fillers, metal oxides and ceramics with organic materials, e.g., resins, in forming interpenetrating polymer networks with organic materials and in crosslinking organic and silicone materials. Most of these silanes include only a primary or secondary amino functionality. However, primary and secondary amine functionalities can be overly reactive in the end use formulation undergoing side reactions and lose efficacy over time.

Moreover, many secondary amines are synthesized by using mono, di or trialkoxy functional silanes. Thus, in aqueous solutions the utility can be compromised by the silanes forming polysiloxanes that are not desirable, e.g., stable cubic structures. These structures adhere poorly.

SUMMARY OF THE INVENTION

Bis-silyl tertiary amines of the formula (I) $[((R^1)_bY)_a R^2_{3-a}SiR^3]_2NX$ wherein $R^1$ and $R^2$ are monovalent radicals, $R^3$ is a divalent radical, X is a monovalent carbonyl containing radical, Y is oxygen, nitrogen or sulfur, a=1 to 3, and b=1 or 2 depending on the valence of Y, provide controlled reactivity and good adhesion.

DETAILED DESCRIPTION OF THE INVENTION STRUCTURE

In formula I above each $R^1$ is a monovalent radical, e.g., hydrogen, a silyl group, an imino group, a dialkyl amine, or, preferably a hydrocarbon functionality, including, but not limited to, aryl, allyl, cycloalkyl, alkyl (linear or branched) or aralkyl that may contain heteroatoms, e.g., oxygen, nitrogen or sulfur. $R^1$ could also be a silyl functionality or an acyl functionality (e.g., trimethoxysilyl, or acetyl). Examples of $R^1$ are $—N{=}C(CH_3)_2$, $—Si(OCH_3)_3$, and $—CH{=}CHCH_3$. Most preferably $R^1$ is an alkyl of 1 to 10 carbon atoms, e.g., methyl, ethyl, isopropyl, cyclohexyl, or t-butyl.

Y is a heteroatom selected from oxygen, nitrogen or sulfur. The value of b depends on the valency of Y, i.e., b=1 for Y=oxygen or sulfur, and b=2 for Y=nitrogen. Preferably Y is oxygen.

Preferably a is 3, but if a<3, each $R^2$ is a monovalent radical, including, but not limited to, a hydrocarbon radical, a saturated hydrocarbon, an unsaturated hydrocarbon or cyano. Preferably $R^2$ is a cycloalkyl, alkyl (linear or branched) or aralkyl, that may include heteroatoms, e.g., oxygen, nitrogen, or sulfur. Exemplary $R^2$ include, phenyl, phenylethyl, 3-oxobutyl or 2-methoxypropyl. Most preferably $R^2$ is methyl or ethyl.

$R^3$ is a divalent bridging group, including, but not limited to an alkylene, alkarylene, arylene, or polyalkylene oxide, but preferably is a $C_1$–$C_{12}$ alkylene, e.g., propylene or butylene, and may be branched, e.g., neopentylene, cyclic, e.g., dimethylene cyclohexane, or unsaturated, e.g., dimethylene cyclohexene. $R^3$ may include a heteroatom substituents, e.g., $R^3$ may include an amino group either in the backbone or pendant to the backbone. If $R^3$ includes an amine functionality, each amine therein is a tertiary amine. Specific examples of $R^3$ are propylene, n-butylene, phenylene, di(ethylene) ethyl amine, and polyoxyethylene.

X is a carbonyl containing monovalent radical, e.g., keto, ester, thioester or amide radical. Preferable embodiments of X may be expressed by the formula (II) $(R^4)_bZC({=}O)CH(Q)CH(Q)$-. Z is $CH_2$, O, S or N (depending on whether X is a keto, ester, thioester or amide, respectively). Q is H, alkyl, aryl, alkaryl, or $(R^4)_bZC({=}O)—$. $R^4$ is a hydrocarbon moiety of one to twenty carbon atoms that may contain heteroatoms, a hydrogen, a silyl, or an organic polymer, e.g., polyester, polyurethane, polyether, polysulfide or polyamide, that itself may contain one or more $ZC({=}O)CHQCHQN[R^3SiR^2_{3-a}(Y(R^1_b)_a]_2$ groups. $R^4$ preferably is an alkyl (linear, cyclic or branched), aryl or alkaryl, and more preferably an alkyl of one to four carbon atoms. Q is preferably hydrogen. The value of b, as in Formula I, depends on the valency of Z, e.g., b=1 for Z=oxygen or sulfur, and b=2 for Z=nitrogen.

Specific examples of X include: $(CH_3)_3COC({=}O)CH_2CH_2—$, $CH_3OC({=}O)CH(CH_3)CH_2—$, $(CH_3CH_2)OC({=}O)CH_2CH(CH_3)—$, $(CH_3)_2CHOC({=}O)CH_2CH(C_6H_5)—$, $CH_3OC({=}O)CH_2CH[C({=}O)OCH_3]—$, $H_2C{=}CHOC({=}O)CH_2CH_2—$, $C_6H_5OC({=}O)CH_2CH_2—$, $C_6H_5CH_2OC({=}O)CH_2CH_2—$, $CH_3C({=}O)(CH_2CH_2O)_5C({=}O)CH_2CH_2—$, $CH_3C({=}O)OC_6H_4OC({=}O)CH_2CH_2—$, $CH_3OC({=}O)CH_2CH(CN)—$, $C_6H_{11}OC({=}O)CH_2CH_2—$, $H_2NC({=}O)CH_2CH_2—$, $(CH_3)_2NC({=}O)CH_2CH_2—$, $(CH_3)_2CHNHC({=}O)CH_2CH_2—$, $H_2C{=}CHCH_2NHC({=}O)CH_2CH_2—$, $CH_3SC({=}O)CH_2CH_2—$, $CH_3(CH_2)_3SC({=}O)CH_2CH_2—$, $C_6H_5SC({=}O)CH_2CH_2—$, $CH_3C({=}O)CH_2CH_2—$, $C_6H_5C({=}O)CH_2CH_2—$, $H_2C{=}CHCH_2C({=}O)CH_2CH_2—$, $CF_3C({=}O)CH_2CH_2—$, $[(CH_3O)_3Si(CH_2)_3]_2NCH_2CH_2C({=}O)O[CH_2CH_2OC({=}O)(CH_2)_4C({=}O)O]_{10}C({=}O)CH_2CH_2—$ Specific examples of the bis(silyl) amines that are useful in the present invention include:

$[(CH_3O)_3Si(CH_2)_3]_2\ NCH_2CH_2C({=}O)OC(CH_3)_3$, $[(CH_3O)_3SiCH_2CH_2CH_2N(CH_2CH_2C({=}O)NH_2)CH_2—]_2$, $[(CH_3)_2CH\ O)_3SiCH_2CH_2\ C_6H_4]_2\ NCH_2CH_2C({=}O)CH_3$, $[(CH_3O)_3SiOSi(OCH_3)_2CH2CH2CH2N(CH_2CH_2C({=}O)NH_2)CH_2—]_2$, $[(CH_3CH_2O)_2Si(CH_3)CH_2CH_2C(CH_3)_2H_2]_2NCH_2CH_2C({=}O)SCH_3$, $[(CH_3)_2C{=}NO)_3SiCH_2CH_2C(CH_3)_2CH_2]_2NCH_2CH_2C({=}O)SCH_3$, $[(CH_3O)_3Si(CH_2)_3]_2NCH_2CH_2C({=}O)O[CH_2CH_2OC({=}O)(CH_2)_4C({=}O)O]_{10}CH_2CH_2OC({=}O)CH_2CH_2N[(CH_2)_3Si(OCH_3)_3]_2$.

Method of Manufacture

The amines of the present invention are made by Michael addition reaction chemistry from the corresponding bis-silyl secondary amine and an αβ-unsaturated carbonyl compound including, but not limited to, ketones, esters, thioesters, amides and organic polymers that contain at least one α,β-unsaturated carbonyl groups, e.g., unsaturated polyesters, unsaturated polyamides or vinyl esters.

The α,β-unsaturated carbonyl containing compound, i.e., $(R^4)_bZC({=}O)CQ{=}CHQ$ wherein $R^4$, Z, Q and b are as in formula (II) above.

Suitable ketones include alkyl vinyl ketones, allyl vinyl ketones, and phenyl vinyl ketones. Suitable esters include acrylate, methacrylate, crotonate, cinnimate, maleate, sorbate, itaconate and fumarate esters of methyl, ethyl, propyl, butyl, phenyl and benzyl. A preferred ester is t-butyl acrylate. The corresponding S or N containing compounds are useful as well. Organic polymers that contain α,β-unsaturated carbonyl functional groups including unsaturated polyesters that are made from condensation of diols with diacids of which some of the diacids contain α,β- unsaturated carbonyls, e.g., fumaric or maleic acid, vinyl esters, and acrylate capped polyethers, polyamides and polysufide polymers.

The bis-silyl amines for the Michael reaction are of the formula (III) $[((R^1)_bY)_aR^2_{3-a}SiR^3]_2NH$ where $R^1$, $R^2$, $R^3$, a, b, and Y are as in Formula I. Specific examples of these silanes are bis-(3-trimethoxysilylpropyl) amine, bis-(3-triethoxysilylpropyl) amine, N-(3-trimethoxysilylpropyl)-N-(4-trimethoxysilylphenyl) amine and bis(-3-triisopropoxysilylpropyl) amine. Such bis-silyl amines are avaiable under the tradename, SILQUEST® A-1170, for bis-(3-trimethoxysilylpropyl) amine from Witco Corporation. Moreover, diamines may be used, wherein each amine would react with an acrylate. For example $((R^1)_bY)_aR^2_{3-a}Si—(CH_2)_n—NH—(CH_2)_n—NH—(CH_2)_n—SiR^2_{3-a}(Y(R^1_b))_a$ wherein each "n" is individually 1 to 10 may be used. Moreover, these amines may be made in the art as taught in U.S. Pat. No. 4,526,996.

The Michael adduct reaction chemistry is known as disclosed in U.S. Pat. No. 4,122,074, which is incorporated herein by reference. The reaction preferably is run at an excess of amine to avoid the presence of unreacted acrylates in the final product. The process may be run with a condensation catalyst. The reaction temperature is 65° to 140° C. and reaction time is typically 6 to 100 hours. The resultant product may be distilled or filtered to purify same.

Utility

The bis-silyl tertiary amines have no active hydrogen on the nitrogen and so may be used in any reaction system where primary and secondary amines otherwise would tend to undergo undesirable side reactions. The tertiary amine is, however, available as a catalyst to increase the rate of silane hydrolysis and crosslinking reactions and to catalyze the reactions of the silyl groups containing a hydrolyzable group or after hydrolysis, silanol groups, with inorganic materials. The bis-silanes have multiple hydrolyzable groups (e.g., alkoxy). The two silyl groups provide for multiple attachments to the inorganic surface of strong, stable bonds and form films with lower amounts of the non-bonding polysiloxanes, e.g. cubic structures. Exemplary applications include films, solvent and aqueous based coatings, adhesives, binders, primers, fiberglass sizes, downhole fine consolidation, foundry, paints and any other application wherein amino silanes have heretofore been used.

The amino silanes of the present invention may be combined with known additives, such as anti-static agents, organic polymers, silylated polymers, siloxanes, lubricants, pigments, fillers (fibrous and non-fibrous), inhibitors, emulsifiers, and other silanes.

EXAMPLES

Michael adduct of bis-(3-trimethoxysilylpropyl) amine and methyl acrylate

1. To a 3 L, 3-neck flask equipped with an addition funnel, Vigreux column, thermometer, gas inlet, magnetic stir bar and heating mantle were bis (3-trimethoxysilylpropyl) amine (901.3 g, 2.64 mol, 1.1 eq) and methanol (479.2 g). The flask was placed under a nitrogen atmosphere using house nitrogen and a bubbler line. The flask was warmed to 50° C. and methyl acrylate (207g, 2.4 mol, 1.0 eq) was added over 1.5 hours via the addition funnel. After 2 days at room temperature, GC analysis showed no remaining methyl acrylate. Methanol was removed under reduced pressure (60° C., 0.1 mm Hg).

Michael adduct of bis (3-trimethoxysilyl propyl) amine and t-butylacrylate

2. To a 2 liter, 3-neck flask equipped with Freidrich condenser, addition funnel, heating mantle, thermometer, PTFE coated stirbar and a gas inlet were charged bis (3-trimethoxysilyl propyl) amine (751.3 g, 2.2 mol, 1 eq) and methanol (402 g). The flask was upheated to 40° C. and placed under a nitrogen atmosphere using house nitrogen and a bubbler line. t-butyl acrylate (253.8 g, 2.0 mol, 0.9 eq.) was added via the addition funnel over 40 minutes. Heat was increased to reflux and held for ca. 6 hours. Methanol was stripped at atmospheric pressure followed by stripping under high vacuum to remove last traces of methanol and acrylate. Product was filtered through a 0.1$\mu$ Abestocel pad. GC-MS analysis indicated the Michael adduct as the major product (ca. 90%). The reaction was run with an excess of amine which accounts for the remaining 10% of the product. The product will be called Amine A.

Michael adduct of bis (3-trimethoxysilylpropyl) amine and n-butylacrylate

3. To a 2 liter, 3-neck flask equipped with Freidrich condenser, addition funnel, heating mantle, thermometer, PTFE coated stirbar and a gas inlet was charged bis (3-trimethoxysilyl propyl) amine(751.3 g, 2.2 mol, 1 eq). Flask was upheated to 40° C. and placed under a nitrogen atmosphere using a bubbler line. n-Butyl acrylate (253.8 g, 2.0 mol, 0.9 eq.) was added via the addition funnel over 25 minutes. Heat was increased to 50° C. for 1 hour followed by 70° C. for 4 hours. GC analysis indicated low conversion. The temperature was increased to 100° C. for 42 hours, 120° C. for 18 hours then 140° C. for 42 hours. Lights were stripped under reduced pressure using a short path distillation head. Product was distilled using a falling film molecular still. Using refluxing 1-octonol as the heat source, crude product was fed into the still at 50 drops/minute at 0.3 mm Hg. GC-MS analysis indicated the Michael adduct as the major product (ca. 90%). The reaction was run with an excess of amine which accounts for the remaining 10% of the product.

Preparation and Physical Testing (Solvent Resistance) of the Films

4. Acrylic polymers were evaluated using a styrene acrylic latex (SCX2500, S. C. Johnson & Son) containing 6% of a coalescent agent diethylene glycol monobutyl ether. The mixture (used for the control) was coated onto 4"×12" aluminum plates and cured at room temperature for 7 days. The film was evaluated using an ASTM D 4752-87 MEK rub test. The control film failed after 10 rubs. 3% of Amine A was added to the control mixture and coated onto an aluminum substrate. The film was cured under the same conditions as the control. The Amine A containing film failed after 24 rubs in the MEK rub test (240% increase over the control).

5. Urethane/acrylic hybrid polymers were evaluated using a urethane hybrid emulsion (Flexane 620, Air Products and Chemicals, Inc.). The neat emulsion, used for the control, was cast onto an aluminum plate and cured at 66° C. for 15 min then at room temperature for 7 days. The film was evaluated using an isopropanol hammer rub (1 pound hammer). The control failed after 80 rubs. Flexane 620 containing 3% of Amine A was cast onto aluminum plates and cured under the same conditions as the control. The film failed after 340 isopropanol hammer rubs (425% increase over the control).

We claim:

1. An amine comprising:

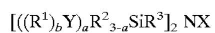

$$[((R^1)_bY)_aR^2_{3-a}SiR^3]_2\ NX$$

wherein $R^1$ and $R^2$ are each monovalent radicals;

$R^3$ is a divalent linking group;

a is 1 to 3;

Y is oxygen, nitrogen or sulfur;

b is 1 or 2 depending upon the valency of Y; and wherein X is $(R^4)_bZC(=O)CH(Q)CH(Q)$- wherein Z is $CH_2$, O, S or N, Q is H, alkyl, aryl, alkaryl, or $C(=O)ZR^4$ and $R^4$ is a hydrocarbon moiety of one to twenty carbon atoms, hydrogen, a silyl group or an organic polymer.

2. An amine according to claim 1 wherein a=3, Y is oxygen and $R^1$ is selected from the group consisting of: aryl, allyl, cycloalkyl, alkyl (linear or branched) or aralkyl.

3. An amine according to claim 1 wherein $R^2$ is selected from the group consisting of: a saturated hydrocarbon, an unsaturated hydrocarbon and cyano.

4. An amine according to claim 1 wherein $R^3$ is a $C_1$–$C_{12}$ alkylene.

5. An amine according to claim 1 wherein $R^4$ is selected from the group consisting of a hydrocarbon moiety of one to twenty carbon atoms, hydrogen, and a silyl group.

6. An amine according to claim 5 wherein Q is H and Z is O.

7. An amine according to claim 6 wherein a=3 and $R^1$ is methyl or ethyl.

8. An amine according to claim 7 wherein $R^3$ is selected from the group consisting of propylene, n-butylene, di(ethylene) ethyl amine, dimethylene cyclohexane, dimethylene cyclohexene and polyoxyethylene.

9. An amine according to claim 5 wherein a=3, Y is oxygen, and $R^1$=methyl, ethyl or silyl.

10. An amine according to claim 9 wherein Q is hydrogen and $R^3$ is an alkylene group.

11. An amine according to claim 1 wherein Y is oxygen.

12. An amine according to claim 1 selected from the group consisting of $(CH_3)_3COC(=O)CH_2CH_2N[CH_2CH_2CH_2Si(OCH_3)_3]_2$ and $H_2NC(=O)CH_2CH_2N[CH_2CH_2CH_2Si(OCH_3)_3]_2$.

13. The reaction product of (a) an α,β-unsaturated carbonyl compound of the formula $(R^4)_bZC(=O)CQ=CHQ$ where Z is $CH_2$, O, S or N, O is H, alkyl, aryl, alkaryl, or $C(=O)Z(R^4)_b$ and $R^4$ is a hydrocarbon moiety of one to twenty carbon atoms, hydrogen, a silyl or an organic polymer and (b) a bis(silyl)amine.

14. The reaction product of claim 13 wherein the bis(silyl) amine is of the formula $[((R^1)_bY)_aR^2_{3-a}SiR^3]_2$ NH where $R^1$ and $R^2$ each are a monovalent radical; $R^3$ is a divalent linking group; Y is oxygen, nitrogen and sulfur; b is 1 or 2; and a=1 to 3.

15. The reaction product according to claim 14 wherein the bis(silyl) amine is $((R^1_b)Y)_aR^2_{3-a}Si—(CH_2)_n—NH—(CH_2)_n—NH—(CH_2)_n—SiR^2_{3-a}(Y(R^1_b))_a$ wherein each "n" is individually 1 to 10.

16. A reaction product according to claim 13 wherein $R^4$ is selected from the group consisting of a hydrocarbon moiety of one to twenty carbon atoms, hydrogen, and a silyl.

17. A process comprising reacting (a) an α,β-unsaturated carbonyl compound; and (b) a bis(silyl)amine.

18. A process according to claim 17 wherein (a) is of the formula $(R^4)_bZC(=O)CQ=CHQ$ wherein Z is $CH_2$, O, S or N, Q is H, alkyl, aryl, alkaryl, or $C(=O)Z(R^4)_b$ and $R^4$ is a hydrocarbon moiety of one to twenty carbon atoms, hydrogen or a silyl.

19. A process according to claim 18 wherein (b) is of the formula $[((R^1)_bY)_aR^2_{3-a}SiR^3]_2$ NH where $R^1$ and $R^2$ each are a monovalent radical; $R^3$ is a divalent linking group; Y is oxygen, nitrogen or sulfur, b is 1 or 2; and a=1 to 3.

20. A process according to claim 19 wherein a stoichiometric excess of amine is used.

* * * * *